United States Patent [19]
Johnson et al.

[11] Patent Number: 5,869,497
[45] Date of Patent: Feb. 9, 1999

[54] METHOD OF TREATING OR AMELIORATING THE SYMPTOMS OF COMMON COLD OR ALLERGIC RHINITIS

[75] Inventors: Kirk Willis Johnson, Camby; David Lloyd Garver Nelson, Carmel; Lee Alan Phebus, Fountaintown, all of Ind.

[73] Assignee: Eli Lilly and Company, Indianapolis, Ind.

[21] Appl. No.: 813,472

[22] Filed: Mar. 7, 1997

Related U.S. Application Data

[60] Provisional application No. 60/014,038 Mar. 15, 1996.
[51] Int. Cl.$^6$ .................................................... A61K 31/44
[52] U.S. Cl. ........................................ 514/278; 514/300
[58] Field of Search ................................ 514/300, 278

[56] References Cited

U.S. PATENT DOCUMENTS

| | | |
|---|---|---|
| 4,374,835 | 2/1983 | Favier et al. . |
| 4,929,621 | 5/1990 | Manoury et al. .................... 514/275 |
| 4,968,802 | 11/1990 | Garbrecht et al. .................... 546/69 |
| 5,229,382 | 7/1993 | Chakrabark et al. . |
| 5,457,115 | 10/1995 | Perregaard et al. . |
| 5,480,885 | 1/1996 | Rucman et al. . |
| 5,563,160 | 10/1996 | Bramm et al. ...................... 514/353 |
| 5,629,317 | 5/1997 | Audia et al. ...................... 514/278 |
| 5,631,265 | 5/1997 | Audia et al. ...................... 514/292 |
| 5,631,268 | 5/1997 | Carr et al. ...................... 514/321 |

FOREIGN PATENT DOCUMENTS

| | | |
|---|---|---|
| 363963 | 4/1990 | European Pat. Off. . |
| 378468 | 7/1990 | European Pat. Off. . |
| 747049 | 12/1996 | European Pat. Off. . |
| WO 93/16081 | 8/1993 | WIPO . |
| WO 96/06601 | 3/1996 | WIPO . |

OTHER PUBLICATIONS

Huang, et al., Yakugaku, 1990, vol. 110, No. 12, pp. 936–942.
Wainscott, et al., J. of Pharm. and Exp. Therap., 276:720–727 (1996).
Chappell, et al., J.Drug Dev. 5(2); 75–81 (1992).
Tonnesen, et al., Allergy, 43, 310–317 (1988).
Tonnesen, et al., Allergy, 42, 447–450 (1987).

*Primary Examiner*—Raymond Henley, III
*Attorney, Agent, or Firm*—Arleen Palmberg

[57] ABSTRACT

This invention provides methods for the treatment or amelioration of the symptoms of the common cold or allergic rhinitis which comprises administering to a mammal in need thereof a 5-HT$_2$ antagonist.

8 Claims, No Drawings

METHOD OF TREATING OR AMELIORATING THE SYMPTOMS OF COMMON COLD OR ALLERGIC RHINITIS

This application claims priority under 35 USC 119 (e) over U.S. Application Ser. No. 60/014,038, filed Mar. 15, 1996.

FIELD OF THE INVENTION

The present invention is directed to the use of 5-HT2 antagonists for treating or ameliorating the symptoms of the common cold or allergic rhinitis.

BACKGROUND OF THE INVENTION

Since the discovery of serotonin (5-hydroxytryptamine, 5-HT) over four decades ago, the cumulative results of many diverse studies have indicated that serotonin plays a significant role in the functioning of the mammalian body, both in the central nervous-system and in peripheral systems as well. Morphological studies of the central nervous system have shown that serotonergic neurons, which originate in the brain stem, form a very diffuse system that projects to most areas of the brain and spinal cord. R. A. O'Brien, *Serotonin in Mental Abnormalities*, 1:41 (1978); H. W. M. Steinbusch, HANDBOOK OF CHEMICAL NEUROANATOMY, Volume 3, Part II, 68 (1984); N. E. Anden, et al., *Acta Physiologica Scandinavia*, 67:313 (1966). These studies have been complemented by biochemical evidence that indicates large concentrations of 5-HT exist in the brain and spinal cord. H. W. M. Steinbusch, *supra*.

With such a diffuse system, it is not surprising that 5-HT has been implicated as being involved in the expression of a number of behaviors, physiological responses, and diseases which originate in the central nervous system. These include such diverse areas as sleeping, eating, perceiving pain, controlling body temperature, controlling blood pressure, depression, schizophrenia, and other bodily states. R. W. Fuller, BIOLOGY OF SEROTONERGIC TRANSMISSION, 221 (1982); D. J. Boullin, SEROTONIN IN MENTAL ABNORMALITIES 1:316 (1978); J. Barchas, et al., *Serotonin and Behavior*, (1973).

Serotonin plays an important role in peripheral systems as well. For example, approximately 90% of the body's serotonin is synthesized in the gastrointestinal system, and serotonin has been found to mediate a variety of contractile, secretory, and electrophysiologic effects in this system. Serotonin may be taken up by the platelets and, upon platelet aggregation, be released such that the cardiovascular system provides another example of a peripheral network that is very sensitive to serotonin. Given the broad distribution of serotonin within the body, it is understandable that tremendous interest in drugs that affect serotonergic systems exists. In particular, receptor-specific agonists and antagonists are of interest for the treatment of a wide range of disorders, including anxiety, depression, hypertension, migraine, compulsive disorders, schizophrenia, autism, neurodegenerative disorders, such as Alzheimer's disease, Parkinsonism, and Huntington's chorea, and cancer chemotherapy-induced vomiting. M. D. Gershon, et al., THE PERIPHERAL ACTIONS OF 5-HYDROXYTRYPTAMINE, 246 (1989); P. R. Saxena, et al., *Journal of Cardiovascular Pharmacology*, 15: Supplement 7 (1990).

Serotonin produces its effects on cellular physiology by binding to specialized receptors on the cell surface. Multiple types of receptors exist for many neurotransmitters and hormones, including serotonin. The existence of multiple, structurally distinct serotonin receptors has provided the possibility that subtype-selective pharmacologic agents can be produced. The development of such compounds could result in new and increasingly selective therapeutic agents with fewer side effects, since activation of individual receptor subtypes may function to affect specific actions of the different parts of the central and/or peripheral serotonergic systems.

An example of such specificity can be demonstrated by using the vascular system as an example. In certain blood vessels, stimulation of certain 5-HT receptors on the endothelial cells produces vasodilation while stimulation of certain 5-HT receptors on the smooth muscle cells produces vasoconstriction.

Currently, the major classes of serotonin receptors ($5\text{-HT}_1$, $5\text{-HT}_2$, $5\text{-HT}_3$, $5\text{-HT}_4$, $5\text{-HT}_5$, $5\text{-HT}_6$, and $5\text{-HT}_7$) contain some fourteen to eighteen separate receptors that have been formally classified based on their pharmacological or structural differences. [For an excellent review of the pharmacological effects and clinical implications of the various 5-HT receptor types, see Glennon, et al., *Neuroscience and Behavioral Reviews*, 14:35 (1990).] discoveries.

One class of serotonin receptors is the $5\text{-HT}_2$. Of this class, several subtypes are known to exist. These subtypes include $5\text{-HT}_{2A}$, $5\text{-HT}_{2B}$ and $5\text{-HT}_{2C}$. The subtype $5\text{-HT}_{2A}$ is located in the vascular smooth muscle, platelets, lung, CNS and gastrointestinal tract. This receptor is thought to be associated with vasoconstriction, platelet aggregation, and bronchoconstriction. The $5\text{-HT}_{2B}$ receptor is localized in the rat lung, stomach fundus, uterus, bladder, and colon. Interesting areas of $5\text{-HT}_{2B}$ receptor localization in the human include, but are not limited to, the brain and blood vessels. Subtype $5\text{-HT}_{2C}$ is located in the CNS with a high density in the choroid plexus.

Pollen has long been recognized as a cause of allergic rhinitis commonly called "hay fever". Pollen contains proteases which induce the release of mediators from mast cells, thereby stimulating IgE biosynthesis. The degranulation of mast cells by IgE results in the release of histamine which leads to an inflammatory response which causes congestion, itching, and swelling of sinuses. Degranulation of mast cells can also be caused by inflammatory neuropeptides, like substance P, released from sensory nerves. The histamine released by mast cells following degranulation can activate sensory nerves increasing the release of inflammatory neuropeptides and sending signals to the brain causing sneezing and the spread of the allergic reaction to other, nearby areas, for example, causing watery eyes. In this way, sensory nerves participate in the inflammation process. Many eosinophils are present in allergic patients with nasal mucus and neutrophils are present in patients with infected mucus.

Antihistamines are drugs commonly utilized which, when taken orally, frequently have a sedative effect. Alternatively, nasal sprays containing cromolyn sodium have been effective as cromolyn acts by blocking the reaction of the allergen with tissue mast cells. Cromolyn is not entirely effective, however, as it apparently does not bind to some of the mediators of inflammation or the activators of IgE biosynthesis that stimulate the degranulation of mast cells and the production of histamine from the mast cells.

Inflammation is a non-specific response of tissues to diverse stimuli or insults and results in the release of materials at the site of inflammation that induce pain. It is now recognized that mast cells, neutrophils, T-cells and sensory nerves are implicated in the pathophysiology of inflammatory skin conditions as well as in other physiological disorders. Mast cells provide the greatest source of histamines in acute inflammation, as well as chymases, after degranulation by IgE.

The "common cold" is a time honored phrase used by both physicians and lay persons alike for the identification of acute minor respiratory illness. Since the identification of rhinovirus in 1956, a considerable body of knowledge has been acquired on the etiology and epidemiology of common colds. It is known that the common cold is not a single entity, but rather is a group of diseases caused by members of several families of viruses, including parainfluenza viruses, rhinoviruses, respiratory syncytial viruses, enteroviruses, and coronaviruses. Much work has been performed in characterizing viruses which cause the common cold. In addition, the molecular biology of rhinoviruses, the most important common cold viruses, is understood in great detail. In contrast, progress on the treatment of common colds has been slow despite these advances. While there are now large numbers of compounds that have been found to exhibit antiviral activity against cold viruses in cell culture, antiviral compounds have had limited effectiveness in patients.

Because of the widespread dissatisfaction with the currently marketed treatments for the common cold and allergic rhinitis within the affected population, there exists a need for a more efficacious and safe treatment. The present invention provides such a treatment.

5-hydroxytryptamine 2 (5-$HT_2$) family of 5-HT receptors, 5-$HT_{2A}$, 5-$HT_{2B}$ and 5-$HT_{2C}$ receptors. These receptors are G-protein linked receptors that are positively coupled to phosphoinositide metabolism, at least in the cloned versions of these receptors. These receptors share sequence homology and have the same pattern of introns and exons. Similarities in the specificity of the receptors for the ligands further indicates the commonality of receptors in this family. While the method of the present invention can employ any of the 5-$HT_2$ receptor subtypes, a more preferred receptor subtype is 5-$HT_{2B}$.

The present invention provides a method for the treatment or amelioration of the symptoms of the common cold or allergic rhinitis which comprises administering to a mammal in need thereof an effective amount of a 5-$HT_2$ receptor antagonist. A more preferred embodiment of the present invention provides a method for the treatment or amelioration of the symptoms of the common cold or allergic rhinitis which comprises administering to a mammal in need thereof an effective amount of a 5-$HT_{2B}$ receptor antagonist.

In recent publications many different 5-$HT_2$ receptor antagonists which can be utilized in the present method have been described.

For instance, U.S. Pat. No. 5,428,036, incorporated herein by reference, describes a group of 5-$HT_2$ antagonists of Formula II:

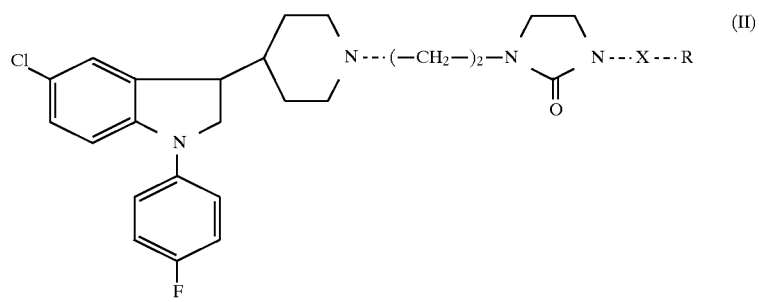

SUMMARY OF THE INVENTION

This invention provides a method for the treatment or amelioration of the symptoms of the common cold or allergic rhinitis in a mammal which comprises administering to a mammal in need thereof an effective amount of a compound having activity as a 5-$HT_2$ antagonist.

DEFINITIONS

The terms and abbreviations used in the instant preparations and examples have their normal meanings unless otherwise designated. For example "°C." refers to degrees Celsius; "N" refers to normal or normality; "mmol" refers to millimole or millimoles; "g" refers to gram or grams; "ml" means milliliter or milliliters; "L" means liter or liters; "M" refers to molar or molarity; "MS" refers to mass spectrometry; "IR" refers to infrared spectroscopy; and "NMR" refers to nuclear magnetic resonance spectroscopy.

The term "allergic rhinitis" as employed herein is understood to include rhinitis medicamentosa, rhinitis sicca, and atrophic rhinitis.

DETAILED DESCRIPTION AND PREFERRED EMBODIMENTS

The method of the present invention employs 5-$HT_2$ receptors. There are three members of the wherein X is selected from CO, CS or $CH_2$, and if X is CO or CS, R is selected from the group consisting of:
i) hydrogen, $C_1$–$C_{24}$ alkyl, $C_2$–$C_{24}$ alkenyl, $C_3$–$C_8$ cycloalkyl, $C_3$–$C_8$ cycloalkenyl or $C_4$–$C_{32}$ cycloalk (en)ylalk(en)yl, optionally substituted with one or two hydroxy groups, or phenyl optionally substituted with one or more substituents selected from the group consisting of halogen, trifluoromethyl, $C_1$–$C_4$ alkyl, $C_1$–$C_4$ alkoxy, $C_1$–$C_4$ alkylthio, acyloxy, or cyano; or
ii) $YR^1$, wherein Y is O or S and $R^1$ is selected from the substituents defined for R under i) above; and
iii) $NR^2R^3$, wherein $R^2$ and $R^3$ independently are selected from the substituents defined for R under i) above or $R^2$ and $R^3$ are combined to form a four to eight member heterocyclic ring containing from one to three nitrogen atoms and from zero to three oxygen or sulfur atoms; or if X is CH2, R is selected from the groups consisting of:
iv) a group $YR^1$ as defined in ii);
v) a group $NR^2R^3$ as defined in iii); or
vi) a group $OC(O)R^4$, wherein $R^4$ is as defined for $R^1$; and pharmaceutically acceptable salts thereof.

Another group of 5-$HT_2$ antagonists include the compounds described in U.S. Pat. No. 5,229,382, incorporated herein by reference, which are of the general Formula III:

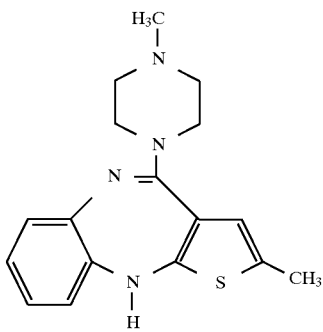

(III)

Still another group of 5-HT$_2$ antagonists are those in U.S. Pat. No. 5,457,115, incorporated herein by reference, which describes antagonists of the Formula IV:

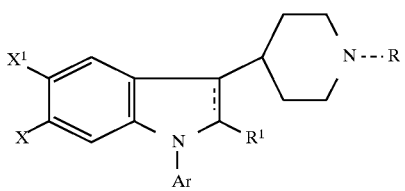

(IV)

where Ar is one of a phenyl group, a phenyl group substituted with at least one substituent selected from halogen, lower alkyl, lower alkoxy, hydroxy, trifluoromethyl, and cyano, and a hetero aromatic group selected from 2-thienyl, 3-thienyl, 2-furanyl, 3-furanyl, 2-oxazolyl, 2-imidazolyl, 2-pyridyl, 3-pyridyl, and 4-pyridyl; each dotted line is an optional double bond; X and $X^1$ are independently selected from the group consisting of hydrogen, halogen, lower alkyl, lower alkoxy, hydroxy, lower alkylthio, lower alkylsulfonyl, lower alkylamino, lower dialkylamino, cyano, trifluoromethyl, and trifluoromethylthio; or X and $X^1$ are taken together to form a 5 to 7 membered carbocyclic ring; $R^1$ is selected from the group consisting of hydrogen, lower alkyl and alkyl substituted with one or two hydroxy groups; with the proviso that when X is hydrogen or fluoro then $R^1$ cannot be hydrogen; R is a substituent having the formula:

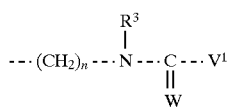

wherein n is an integer from 2–6 inclusive; W is oxygen or sulfur; $V^1$ is selected from $OR^4$, $SR^5$, $CHR^6R^7$, and $NR^8R^9$;

wherein $R^3$ to $R^9$ are independently selected from the group consisting of hydrogen, lower alkyl, lower alkenyl, cycloalkyl, lower alkyl substituted with one or two hydroxyl groups; and lower alkenyl substituted with one or two hydroxyl groups; and pharmaceutically acceptable acid addition salts or prodrugs thereof.

An even further group of 5-HT$_2$ antagonists which can be utilized in the present method include those in U.S. Pat. No. 5,480,885, incorporated herein by reference, which describes antagonists of the Formula V:

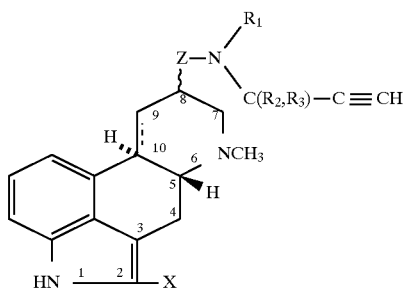

(V)

wherein $R_1$, $R_2$ and $R_3$ independently represent a hydrogen atom or a straight-chain or branched-chain $C_1$–$C_6$ alkyl group, X represents a hydrogen or a halogen atom;

Z represents a carbonyl or methylene group and $C_9$=$C_{10}$ represents a single or a double bond, racemates and acid addition salts thereof.

The above groups of compounds are only illustrative of the 5-HT$_2$ receptor antagonists which are currently under development. This listing of groups of compounds is not meant to be comprehensive, the methods of the present invention may employ any 5-HT$_2$ receptor antagonist and is not limited to any particular class of compound.

A more preferred class of antagonists are the 5-HT$_2$ receptor antagonists of Formula VI:

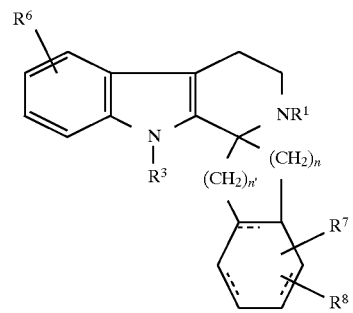

(VI)

wherein
$R^1$ is hydrogen or $C_1$–$C_3$ alkyl;
$R_3$ is hydrogen or $C_1$–$C_3$ alkyl;
$R^6$ is selected from the group consisting of hydrogen, $C_1$–$C_6$ alkyl, $C_2$–$C_6$ alkenyl, halo, halo($C_1$–$C_6$)alkyl, halo($C_2$–$C_6$)alkenyl, $COR^5$, $C_1$–$C_{10}$ alkanoyl, $CO_2R^{5'}$, ($C_1$–$C_6$ alkyl)$_m$amino, $NO_2$, —$SR^5$, and $OR^5$;
$R^7$ and $R^8$ are independently selected from the group consisting of hydrogen, $C_1$–$C_6$ alkyl, $C_2$–$C_6$ alkenyl, $NO_2$, halo, halo($C_1$–$C_6$)alkyl, halo($C_2$–$C_6$)alkenyl, $COR^5$, $C_1$–$C_{10}$ alkanoyl, $C_7$–$C_{16}$ arylalkyl, $CO_2R^{5'}$, ($C_1$–$C_6$ alkyl)$_m$amino, —$SR^5$, and $OR^5$;
n is 1, 2, or 3;
n' is 1, 2, or 3;
m is 1 or 2;
$R^5$ is independently hydrogen or $C_1$–$C_4$ alkyl;
$R^{5'}$ is $C_1$–$C_4$ alkyl;
— is optionally a bond;
a pharmaceutically acceptable salt or solvate thereof.

Examples of compounds of Formula VI include but are not limited to: spiro-9,9[2-(3,4-dichloro)-1,2,3,4-tetrahydronaphthyl]-5-methoxy-1,2,3,9-tetrahydro-8H-pyrido indole, spiro-9,9[2-(3,4-dimethoxy)-1,2,3,4-tetrahydronaphthyl]-5-methyl-1,2,3,9-tetrahydro-8H-pyrido indole, spiro-9,9[2-(3,4-diethoxy)-1,2,3,4-tetrahydronaphthyl]-5-methyl-1,2,3,9-tetrahydro-8H-pyrido indole, spiro-9,9[2-(3,5-dichloro)-1,2,3,4- tetrahydronaphthyl]-5-dimethylamino-1,2,3,9-tetrahydro-8H-pyrido indole, spiro-9,9[2-(3-fluoro,4-chloro)-1,2,3,4-tetrahydronaphthyl]-5-ethyl-1,2,3,9-tetrahydro-8H-pyrido indole, spiro-9,9[2-(3,4-dimethoxy)-1,2,3,4-indole, spiro-9,9[2-(3,4-dimethoxy)-1,2,3,4-tetrahydronaphthyl]-5-bromo-1,2,3,9-tetrahydro-8H-pyrido indole, spiro-9,9[2-(3,4-dimethoxy)-1,2,3,4-tetrahydronaphthyl]-5-chloro-1,2,3,9-tetrahydro-8H-pyrido indole.

The synthesis of these compounds is described in co-pending United States Provisional Patent Application Ser. No. 06/014,119, Attorney Docket No. P-10656, filed Mar. 25, 1996, incorporated herein by reference. The syntheses of typical compounds from this class, including six specific examples, are detailed infra.

The compounds of Formula VI can be prepared using chemical processes that are understood in the art. The examples are illustrative only, and are not intended to limit the scope of the invention.

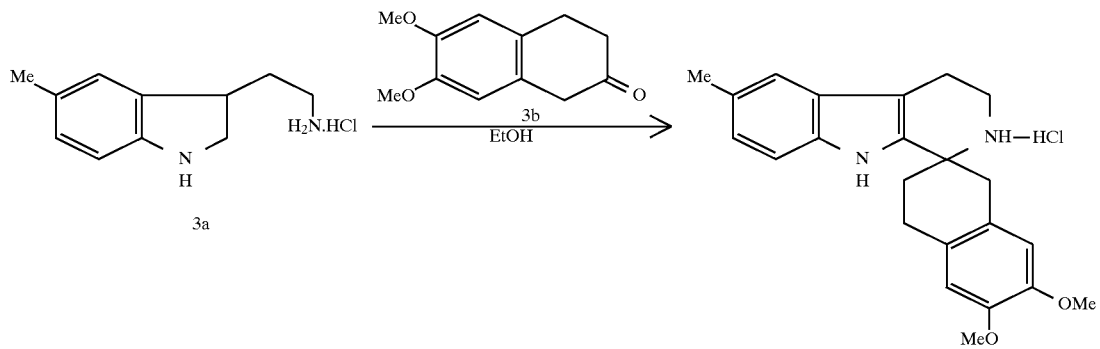

Indole Starting Materials

The indole starting materials (1a, 1b, and 1c) infra. were purchased (1a), prepared according to Bartoli's procedure (1b) [G. Bartoli, et al., *Tetrahedron Lett.*, 1989, 30, 2129] or (1c) synthesized from 2-Iodo-4,6-dimethylaniline (5'''). The process is illustrated by the following Scheme:

Scheme IV

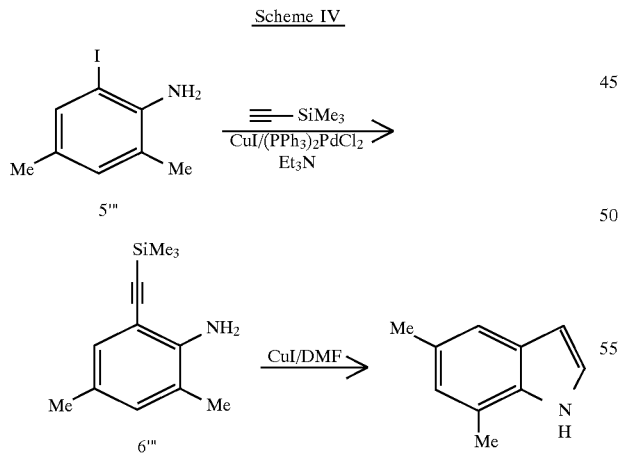

The 2-Iodo-4,6-dimethylaniline (5''') synthesis can be completed as follows: To a suspension of 5''' (24 mmol.), CuI (0.05 equiv.) and (PPh$_3$)$_2$PdCl$_2$ (0.05 equiv.) in 30 ml of dry triethylamine under Ar. atmosphere was added trimethylsilylacetylene (1.1 equiv.) and the resulting mixture was stirred for 3 hours. Then, the solvent was eliminated under vacuum and the residue purified by flash chromatography using hexane/ethyl acetate (3:1) as eluent to yield 6''' in quantitative yield. A slurry of 6''' (23 mmol.) and CuI (2 equiv.) in 50 ml of dry dimethyl formamide was heated for 2.5 h. under Ar. atmosphere at 100° C. After cooling down to room temperature the reaction mixture was filtered off and the solid washed twice with ether (20 ml.). The organic phase was washed with water (3×50 ml.), dried over Na$_2$SO$_4$ and the solvent evaporated to dryness. The crude product was purified by flash chromatography using hexane/ethyl acetate (3:1) as eluent to afford 1c (1.5 g., 45%).

EXAMPLE 1

A suspension of the corresponding tryptamine hydrochloride (3a) (1 gram) and the corresponding dimethoxytetralone (3b) (1 gram) in ethanol (10 ml.) was refluxed during 128 h. After this time the reaction mixture was allowed to reach room temperature and filtered off. The crude solid was washed and dried. Melting point 261° C.

|   | Theory | Found |
|---|--------|-------|
| C | 69.25  | 69.34 |
| H | 6.82   | 6.97  |
| N | 7.02   | 6.98  |

EXAMPLE 2

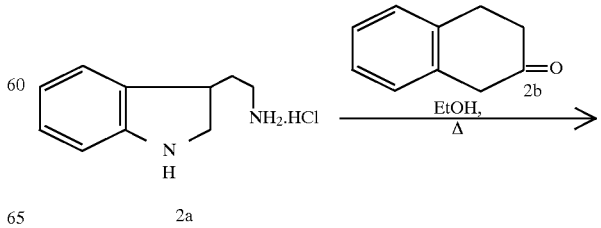

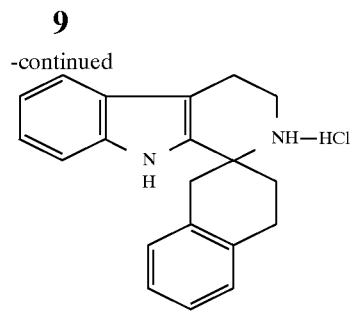

A suspension of the corresponding tryptamine hydrochloride (2a) (575 mg) and the corresponding ketone (2b) (464 mg) in ethanol (10 ml.) was refluxed during 128 h. After this time the reaction mixture was allowed to reach room temperature and filtered off. The crude solid was washed and dried.

Yield: 525 mg

|   | Theory | Found |
|---|--------|-------|
| C | 74.43  | 74.36 |
| H | 6.84   | 6.84  |
| N | 8.27   | 8.25  |

MS: 301

EXAMPLE 3

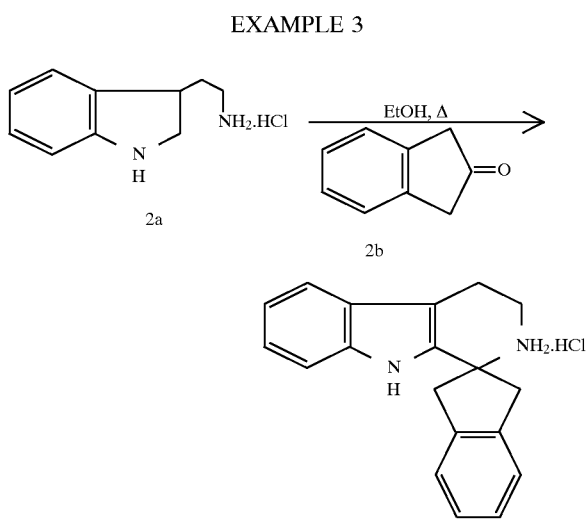

A suspension of the corresponding tryptamine hydrochloride (2a) (500 mg) and the corresponding ketone (2b) (396 mg) in ethanol (10 ml.) was refluxed during 72 h. After this time the reaction mixture was cooled to about 0° C. and filtered off. The crude solid was washed and dried.

Yield: 262 mg

MS: 274

EXAMPLE 4

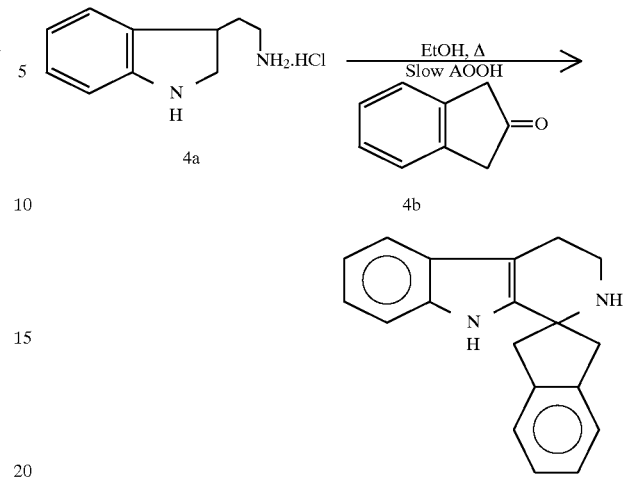

A suspension of the corresponding tryptamine hydrochloride (4a) (500 mg) and the corresponding ketone (4b) (396 mg) in ethanol (10 ml.) was refluxed during 72 h. After this time the reaction mixture was cooled to about 0° C. for about 24 hours and filtered off. The crude solid was washed and dried.

Submitted for mass spectral analysis and found mi of 274.

EXAMPLE 5

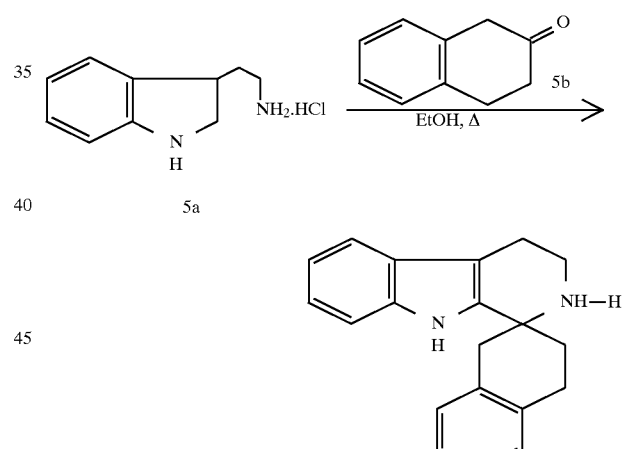

A suspension of the corresponding tryptamine hydrochloride (5a) (500 mg) and the corresponding ketone (5b) (397 μL) in ethanol (10 ml.) was refluxed during 72 h. After this time the reaction mixture was cooled to about 0° C. for 14 hours and filtered off. The crude solid was washed and dried.

Yield: 630 mg

|   | Theory | Found |
|---|--------|-------|
| C | 73.95  | 73.32 |
| H | 6.52   | 6.73  |
| N | 8.62   | 8.59  |

MS: 288

EXAMPLE 6

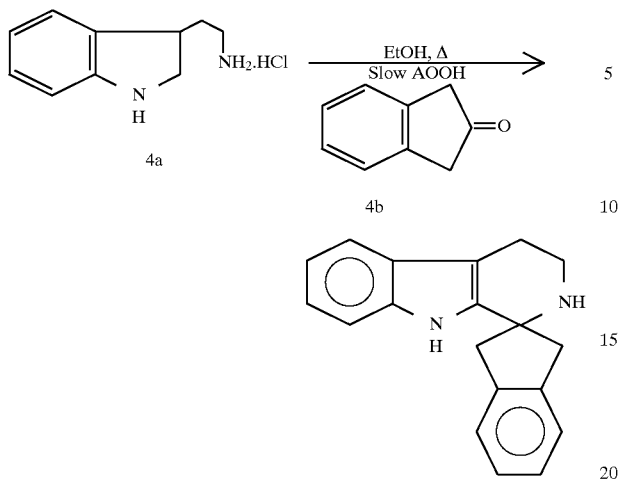

A suspension of the corresponding tryptamine hydrochloride (4a) (1 g) and the corresponding ketone (4b) (800 mg) in ethanol (10 ml.) was refluxed during 72 h. After this time the reaction mixture was cooled to about 0° C. for about 24 hours and filtered off. The crude solid was washed and dried.

Yield: 550 mg

|   | Theory | Found |
|---|--------|-------|
| C | 70.67  | 70.88 |
| H | 7.06   | 7.16  |
| N | 7.85   | 7.88  |

An additional preferred class of 5-HT$_2$ receptor antagonists are those compounds described in WO 95/24200, incorporated herein by reference, which are of Formula I:

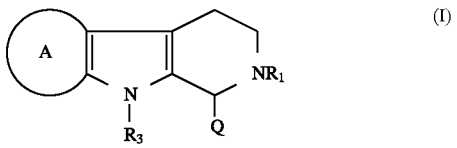

wherein

Q is hydrogen or $(CHR_2)R_4$;

$R_1$ is hydrogen or $C_1$–$C_3$ alkyl;

$R_2$ is hydrogen or $C_1$–$C_3$ alkyl;

$R_3$ is hydrogen or $C_1$–$C_3$ alkyl;

$R_4$ is $C_5$–$C_8$ cycloalkyl, substituted $C_5$–$C_8$ cycloalkyl, $C_5$–$C_8$ cycloalkenyl, substituted $C_5$–$C_8$ cycloalkenyl, bicyclic or substituted bicyclic;

A is selected from the group consisting of

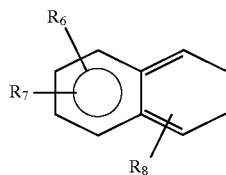

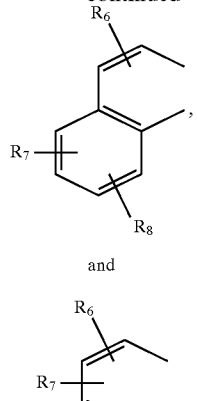

wherein, $R_6$ and $R_7$ are, independently, hydrogen, $C_1$–$C_6$ alkyl, $C_2$–$C_6$ alkenyl, halo, halo($C_1$–$C_6$) alkyl, halo($C_2$–$C_6$) alkenyl, $COR_5$, $C_1$–$C_{10}$ alkanoyl, $CO_2R_5'$, ($C_1$–$C_6$ alkyl)$_m$ amino, $NO_2$, —$SR_5$, or $OR_5$;

m is 1 or 2;

$R_5$ is independently hydrogen or $C_1$–$C_4$ alkyl;

$R_5'$ is $C_1$–$C_4$ alkyl;

$R_8$ is independently selected from the group consisting of an $R_6$ group, substituted $C_3$–$C_8$ cycloalkyl, $C_3$–$C_8$ cycloalkyl, $C_3$–$C_8$ cycloalkyl-($C_1$–$C_3$)alkyl, $C_5$–$C_8$ cycloalkenyl, substituted $C_5$–$C_8$ cycloakenyl, $C_5$–$C_8$ cycloalkenyl-($C_1$–$C_3$)alkyl, $C_7$–$C_{16}$ arylalkyl; or $R_6$ and $R_7$ together with the carbon atoms of group A form a 5- to 8-member carbon ring; or a pharmaceutically acceptable salt or solvate thereof.

Examples of compounds of Formula I include but are not limited to: 8-methyl-1-[3,4-dimethoxyphenyl)methyl]1,2,3,4-tetrahydro-9H-pyrido[3,4-b]indole, 8-bromo-1-[3,4-dimethoxyphenyl)methyl]-1,2,3,4-tetrahydro-9H-pyrido[3,4-b]indole hydrochloride, 6,8-dibromo-1-[3,4-dimethoxyphenyl)methyl]-1,2,3,4-tetrahydro-9H-pyrido[3,4-b]indole; 6-methyl-8-bromo-1-[3,4-dimethoxyphenyl)-methyl]-1,2,3,4-tetrahydro-9H-pyrido[3,4-b]indole hydrochloride; 8-methoxy-1-[3,4-dimethoxyphenyl)methyl]-1,2,3,4-tetrahydro-9H-pyrido[3,4-b]indole; 6,8-difluoro-1-[(3,4-dimethoxyphenyl)-methyl]-1,2,3,4-tetrahydro-9H-pyrido[3,4-b]indole; 7-methyl-8-bromo-1-[3,4-dimethoxyphenyl)-methyl]-1,2,3,4-tetrahydro-9H-pyrido[3,4-b]indole hydrochloride; 6-(1,1-dimethylethyl)-1-[(3,4-dimethoxyphenyl)methyl]1,2,3,4-tetrahydro-1-9H-pyrido-[3,4b]indole hydrochloride; 5-fluoro-6-methyl-1-[(3,4-dimethoxyphenyl)-methyl]-1,2,3,4-tetrahydro-9H-pyrido[3,4-b]indole; 7,8,9,10-tetrahydro-10-[(3,4-dimethoxyphenyl)methyl]-11H-benzo[g]pyrido[3,4-b]indole; 6-cyclohexyl-1-[(3,4-dimethoxyphenyl)-methyl]-1,2,3,4-tetrahydro-9H-pyrido[3,4-b]indole hydrochloride; 5,8-dimethyl-1,2,3,4-tetrahydro-1-[(3,4-dimethoxyphenyl)methyl]-9H-pyrido[3,4b]indole hydrochloride; 6-(1-methylethyl)-1,2,3,4-tetrahydro-1-[(3,4-dimethoxyphenyl)methyl]-9H-pyrido[3,4b]indole; 6,8-dimethyl-1,2,3,4-tetrahydro-1-[(3,4-dimethoxyphenyl)methyl]-9H-pyrido[3,4b]indole hydrochloride; 5,7-dimethyl-1,2,3,4-tetrahydro-1-[(3,4-dimethoxyphenyl)methyl]-9H-pyrido[3,4b]indole hydrochloride; 6,7-dimethyl-1,2,3,4-tetrahydro-1-[(3,4-dimethoxyphenyl)methyl]-9H-pyrido[3,4b]indole; 6-ethyl-1,2,3,4-tetrahydro-1-[(3,4-dimethoxyphenyl)methyl]-9H- pyrido[3,4b]indole; 6-bromo-1,2,3,4-tetrahydro-1-[(3,4-dimethoxyphenyl)methyl]- 9H-pyrido[3,4b]indole; 7,8-dimethyl-1,2,3,4-tetrahydro-1-[(3,4-dimethoxyphenyl)methyl]-9H-pyrido[3,4b]indole hydrochloride; 6-methyl-1,2,3,4-tetrahydro-1-[(3,4-dimethoxyphenyl)methyl]-9H-pyrido[3,4b]indole hydrochloride; 6-methyl-1-[(3,4,5-trimethoxyphenyl)-methyl]-1,2,3,4-tetrahydro-9H-pyrido[3,4-b]indole hydrochloride; 6-methyl-1-[(2,3,4-trimethoxyphenyl)-methyl]-1,2,3,4-tetrahydro-9H-pyrido[3,4-b]indole hydrochloride; 6-methyl-1-[(2-methoxyphenyl)methyl]-1,2,3,4-tetrahydro-9H-pyrido[3,4-b]indole hydrochloride; 6-methyl-1-[(2,4-dimethoxyphenyl)methyl]-1,2,3,4-tetrahydro-9H-pyrido[3,4-b]indole hydrochloride; 6-methyl-1-[(2,5-dimethoxyphenyl)methyl]-1,2,3,4-tetrahydro-9H-pyrido[3,4-b]indole hydrochloride; 6-methyl-1-[(2,4,5-trimethoxyphenyl)-methyl]-1,2,3,4-tetrahydro-9H-pyrido[3,4-b]indole hydrochloride; 6-(1-methylethyl)-1-[(2,3,4-trimethoxy-phenyl)methyl]-1,2,3,4-tetrahydro-9H-pyrido[3,4-b]indole hydrochloride; 6-methyl-1-[(3,4-dimethoxy-5-nitrophenyl)-methyl]-1,2,3,4-tetrahydro-9H-pyrido[3,4-b]indole hydrochloride; 6-methyl-1-[(3-iodo-4,5-dimethoxy-phenyl)-methyl]-1,2,3,4-tetrahydro-9H-pyrido[3,4-b]indole; 6-methyl-1-[(3,4-dimethoxy-5-amino-phenyl)-methyl]-1,2,3,4-tetrahydro-9H-pyrido[3,4-b]indole dihydrochloride; 6-methyl-1-[(3-methoxy-4-propoxyphenyl)-methyl]-1,2,3,4-tetrahydro-9H-pyrido[3,4-b]indole; 6-methyl-1-[(4-dimethylaminophenyl)methyl]-1,2,3,4-tetrahydro-9H-pyrido[3,4-b]indole dihydrochloride; 6-methyl-1-[(4-dibutylaminophenyl)methyl]-1,2,3,4-tetrahydro-9H-pyrido[3,4-b]indole dihydrochloride; 6-methyl-1-[(3-fluoro-4-methoxyphenyl)-methyl]-1,2,3,4-tetrahydro-9H-pyrido[3,4-b]indole hydrochloride; 6-(1-methyl-1-[(3,4-dimethylphenyl)methyl]-1,2,3,4-tetrahydro-9H-pyrido[3,4-b]indole hydrochloride; 6-methyl-1-[(2-chloro-3,4-dimethoxyphenyl)-methyl]-1,2,3,4-tetrahydro-9H-pyrido[3,4-b]indole hydrochloride; 6-methyl-1-[(2-chloro-3-methoxy-4-hydroxyphenyl)methyl]-1,2,3,4-tetrahydro-9H-pyrido[3,4-b]-indole hydrochloride; 5-fluoro-6-methyl-1-[(2-chloro-3,4-dimethoxyphenyl)methyl]- 1,2,3,4-tetrahydro-9H-pyrido[3,4-b]indole hydrochloride; 6-methyl-1-(cyclohexylmethyl)-1,2,3,4-tetrahydro-9H-pyrido[3,4-b]indole hydrochloride; 6-methyl-1-[(2-bromo-3,4-dimethoxyphenyl)-methyl]-1,2,3,4-tetrahydro-9H-pyrido[2,4-b]indole; and 6-iodo-1-[(3,4-dimethoxyphenyl)-methyl]-1,2,3,4-tetrahydro-9H-pyrido[3,4-b]indole hydrochloride.

EXAMPLE 7

Preparation of 6-methyl-1-[(2-chloro-3,4-dimethoxyphenyl)-methyl]-1,2,3,4-tetrahydro-9H-pyrido[3,4-b]indole hydrochloride

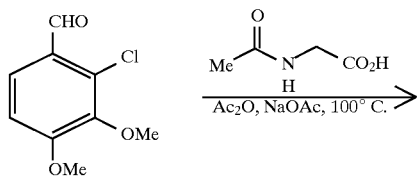

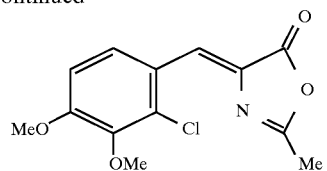

A solution of 2-chloro-3,4-dimethoxybenzaldehyde (10.45 g), N-acetylglycine (11.9 g, 0.10 mol.) and sodium acetate (8.4 g, 0.1 mol) in acetic anhydride (100 mL) was heated to 100° C. for 2 hours. The reaction mixture was cooled to ambient temperature poured onto ice (300 mL) with stirring. The product was isolated by filtration, washed with water (3×50 mL) and diethyl ether (3×50 mL) and dried under reduced pressure (5.26 g).

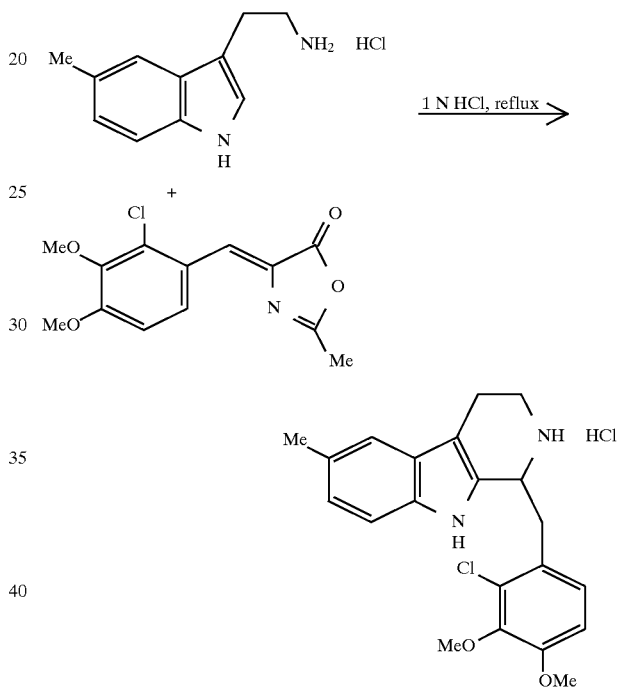

A suspension of azalactone prepared above (1.34 g, 4.76 mmol.) and 5-methyltryptamine hydrochloride (1.0 g, 4.75 mmol.) in 1N HCl (30 mL) was heated to reflux for 24 hours under nitrogen atmosphere. The reaction mixture was cooled to ambient temperature and the crude product isolated by filtration. The solid was triturated with ethanol and washed with diethyl ether. The product was isolated by filtration (1.19 g). m/e=370, mp. 244° C. (dec.).

| Analysis | Calculated | Found |
|---|---|---|
| C | 61.92 | 61.67 |
| H | 5.94 | 5.94 |
| N | 6.88 | 6.94 |

EXAMPLE 8

Preparation of 6-methyl-1-[(2-bromo-3,4-dimethoxyphenyl)-methyl]-1,2,3,4-tetrahydro-9H-pyrido[3,4-b]indole Example 8 was prepared in the same manner as described in Example 7 with the following exception: 2-bromo-3,4- dimethoxybenzaldehyde was used as starting material instead of 2-chloro-3,4-dimethoxybenzaldehyde. The final compound

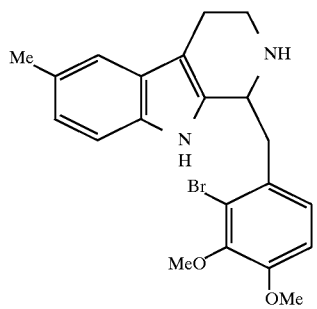

had a yield of 79.2%; M/I 416, 414; and mp 272°–4° C.

| Analysis | Calculated | Found |
|---|---|---|
| C | 55.83 | 55.57 |
| H | 5.35 | 5.36 |
| N | 6.20 | 6.09 |

EXAMPLE 9

Preparation of 6-iodo-1-[(3,4-dimethoxyphenyl)-methyl]-1,2,3,4-tetrahydro-9H-pyrido[3,4-b]indole hydrochloride Example 9 was prepared in the same manner as Example 7 with the following exceptions: 3,4-dimethoxybenzaldehyde was used instead of 2-chloro-3,4-dimethoxybenzaldehyde and 5-iodo-tryptamine instead of 5-methyl-tryptamine as starting materials. Upon completion of the reaction, the mixture was neutralized with aqueous potassium carbonate solution and extracted with chloroform. The combined chloroform phases were dried over anhydrous sodium carbonate and concentrated under reduced pressure. The product was purified by chromatography on silica gel, eluting with 2% methanol in chloroform. Fractions containing product were pooled and concentrated. The residue was dissolved in diethyl ether and was treated with gaseous HCl. The resulting HCl salt was isolated by filtration and dried under reduced pressure. The final compound

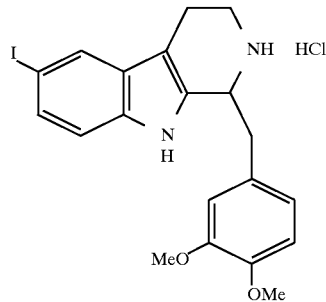

had a yield of 31.3%; M/I 448; and mp 270°–3° C.

| Analysis | Calculated | Found |
|---|---|---|
| C | 49.55 | 49.62 |
| H | 4.57 | 4.51 |
| N | 5.78 | 5.66 |

The biological efficacy of a compound believed to be effective as a 5-HT$_2$ receptor antagonist was confirmed by first employing an initial screening assay which rapidly and accurately measures the binding of the test compound to the 5-HT$_2$ receptor. Once the binding of the test compound is established, the in vivo activity of the test compound on the receptor is established. Assays useful for evaluating 5-HT$_2$ antagonist are well known by those skilled in the art. Assays for each of the 5-HT$_2$ receptors are included below.

5-HT$_{2B}$ Receptor Binding Activity

The ability of a compound to bind to a 5-HT$_{2B}$ receptor was measured using standard procedures such as that listed below.

Assay Procedure.

Certain compounds and intermediates of the present invention are useful for modulating 5-HT$_{2B}$ receptors. The compounds which are most useful for binding a 5-HT$_{2B}$ receptor can be identified using the following procedures. Further, a useful in vivo model for demonstrating 5-HT$_{2B}$ activity is provided infra.

Radioligand Binding Studies for 5-HT$_{2B}$; Membrane preparation from transformed cells Suspension cells expressing the cloned rat 5-HT$_{2B}$ receptor were harvested by centrifugation at 2,200×g for 15 min at 4° C. J. D. Kursar, et al, Mol. Pharmacol., 42:549–557 (1992). Membranes for the binding assays were prepared by vortexing the pellet in 50 mM Tris-HCl, pH 7.4 (0.5×10$^9$ cells/30 ml). The tissue suspension was then centrifuged at 39,800×g for 10 min at 4° C. This procedure was repeated for a total of three washes, with a 10 minute incubation at 37° C. between the first and second wash. The final pellet was homogenized in 67 mM Tris-HCl, pH 7.4 (at 20–40 and 12.5 million cells/ml, original cell number, for cells expressing low and relatively high levels of the 5-HT$_{2B}$ receptor, respectively) using a Tissumizer (Tekmar, Cincinnati, Ohio), setting 65 for 15 seconds.

[$^3$H]5-HT binding studies

Binding assays were automated using a Biomek 1000 (Beckman Instruments, Fullerton, Calif.) and were performed in triplicate in 0.8 ml total volume. Membrane suspension, 200 μl, (0.04–0.27 mg protein) and 200 μl of drug dilution in water were added to 400 μl of 67 mM Tris-HCl, pH 7.4, containing [$^3$H]5-HT, pargyline, CaCl$_2$, and L-ascorbic acid. Final concentrations of pargyline, CaCl$_2$ and L-ascorbic acid were 10 μM, 3 mM and 0.1%, respectively. Tubes were incubated at 37° C. for 15 min or at 0° C. for 2 hours (binding equilibria were verified for both of these conditions), then rapidly filtered using a Brandel cell harvester (Model MB-48R; Brandel, Gaithersburg, Md.) through Whatman GF/B filters which had been presoaked in 0.5% polyethylenimine and precooled with ice-cold 50 mM Tris-HCl, pH 7.4. The filters were then washed rapidly four times with one ml ice-cold 50 mM Tris-HCl, pH 7.4. The amount of [$^3$H]5-HT trapped on the filters was determined by liquid scintillation spectrometry (Ready Protein and Beckman LS 6000IC, Beckman Instruments, Fullerton, Calif.). For the saturation experiments, actual free radioligand concentrations were determined by sampling the supernatant of parallel saturation experiments in which bound radioactivity had been separated by centrifugation. The concentration of [$^3$H]5-HT ranged from 0.02 to 5 nM and 0.6 to 63 nM for saturation experiments incubated at 0° C. and 37° C., respectively. 5-HT, 10 µM, or 1-naphthylpiperazine (1-NP), 10 µM, defined nonspecific binding. For competition experiments, six to twelve concentrations of displacing drugs were used, spanning six log units, and the final concentration of [$^3$H]5-HT was 2 nM. Protein was determined by the method of Bradford, using bovine serum albumin as the standard. M. M. Bradford, *Anal. Biochem.,* 72:248–254 (1976).

Statistical Analysis

The $K_d$ and $B_{max}$ values from the saturation assays were determined for best fit to a one-site or a two-site binding model using a partial F-test. A. De Lean, et al, *Mol. Pharmacol.,* 21:5–16 (1981). The following equation was used for a one-site binding model, $$Bound = \frac{B_{max} \times [L]}{K_d + [L]}$$

where Bound=amount of [$^3$H]5-HT specifically bound, $B_{max}$=maximum number of binding sites, $K_d$=equilibrium dissociation constant and [L]=free concentration of [$^3$H]5-HT, or a two-site binding model, $$Bound = \frac{B_{max1} \times [L]}{K_{d1} + [L]} + \frac{B_{max2} \times [L]}{K_{d2} + [L]}$$

where Bound=amount of [$^3$H]5-HT specifically bound, $B_{max}$=maximum number of high affinity binding sites, $B_{max2}$=maximum number of low affinity binding sites, $K_{d1}$=equilibrium dissociation constant for the high affinity site, $K_{d2}$=equilibrium dissociation constant for the low affinity site and [L]=free concentration of [$^3$H]5-HT. The $IC_{50}$ values from the competition assays, the binding parameters for the $IP_3$ standard curve and the $EC_{50}$ and $E_{max}$ values from the $IP_3$ assays were determined by nonlinear regression analysis of four parameter logistic equations (Systat, Systat Inc, Evanston, Ill.). A. De Lean, et al, *Mol. Pharmacol.,* 21:5–16 (1981). The $IC_{50}$ values were converted to $K_i$ values using the Cheng-Prusoff equation. Y. Cheng, et al, *Biochem. Pharmacol.,* 22:3099–3108 (1973).

Assay Methods 5-HT$_{2B}$ in vitro

Male Wistar rats (150–375 g; Laboratory Supply, Indianapolis, Ind.) were sacrificed by cervical dislocation, and longitudinal section of the stomach fundus were prepared for in vitro examination. Four preparations were obtained from one rat fundus. Ring preparations of the extracted jugular vein were prepared as described by Hooker; *Blood Vessels,* 14:1 (1977) and M. L. Cohen, *J. Pharmacol. Exp. Ther.* 227:327 (1983). Tissues were mounted in organ baths containing 10 mL of modified Krebs solution of the following composition (millimolar concentrations): NaCl, 118.2; KCl, 4.6; $CaCl_2.H_2O$, 1.6; $KH_2PO_4$, 1.2; $MgSO_4$, 1.2; dextrose, 10.0; and $NaHCO_3$, 24.8. Tissue bath solutions were maintained at 37° C. and equilibrated with 95% $O_2$ and 5% $CO_2$. Tissues were placed under optimum resting force (4 g) and were allowed to equilibrate for approximately 1 hour before exposure to the test compound. Isometric contractions were recorded as changes in grams of force on a Beckman Dynograph with Statham UC-3 transducers.

Determination of Apparent Antagonist Dissociation Constant

Noncumulative contractile concentration-response curves for serotonin in the fundus and cumulative concentration response curves in the jugular vein were obtained by a stepwise increase in concentration after washing out the preceding concentrations every 15–20 minutes. Each agonist concentration remained in contact with the tissue for approximately 2 minutes and maximum response to each compound concentration was measured. $ED_{50}$ values were taken as the concentration of agonist that produced half-maximal contraction. After control responses were obtained, tissues were incubated with an appropriate concentration of buffer or antagonist for 1 hour. Responses to serotonin were then repeated in the presence of an antagonist. Concentration responses utilized only one agonist and one antagonist concentration per tissue. In general, successive agonist responses in the presence of buffer treatment were unaltered (average dose ratio was 1.28±0.21).

Apparent antagonist dissociation constants ($K_B$) were determined for each concentration of antagonist according to the following equation:

$$K_B=[B]/(\text{dose ratio-1})$$

where [B] is the concentration of the antagonist and dose ratio is the $ED_{50}$ of the agonist in the presence of the antagonist divided by the control $ED_{50}$. Generally, parallel shifts in the concentration-response curves occurred in the presence of antagonists. The results were expressed as the negative logarithm of the $K_B$ (i.e., -log $K_B$). Calculations were completed using known methods. B. R. Zaborowsky, *J. Pharmacol. Methods,* 4:4165 (1980).

$IP_3$ Formation in 5-HT$_{2B}$ Transformed Cells

Formation and Extraction of $IP_3$: A600K-2-3-MTX cells, grown in suspension, were harvested by centrifugation at 200×g and were resuspended in protein-free cell culture medium. After incubations of the cells (2.5–3×106 cells/tube in 125 µl) at 37° for 10 minutes, 125 µl of the compound of interest, diluted in protein-free medium, were added. All incubations were performed in triplicate. When antagonists were used to inhibit the effect of 5-HT, the cells were incubated with the antagonists for 10 minutes at 37° before the addition of 5-HT. After addition of agonist, the cell suspension was vortexed and incubated for an additional 10 seconds at 37° (the 10 seconds include the time for vortexing). Then 250 µl of ice-cold 10% perchloric acid were added to terminate the reaction. The tubes were incubated for 10 minutes on ice and then centrifuges at 1500×g for 10 minutes. After centrifugation, 400 µl of the supernatant were sampled. The following $IP_3$ extraction procedure was modified from published procedures (E. S. Sharps, et al, A High Performance Liquid Chromatographic Method To Measure $^{32}$P Incorporation Into Phosphorylated Metabolites In Cultured Cells., *Anal. Biochem.* 124:421–424 (1982) and K. A. Wreggett, et al, A Rapic Separation Method For Inositol Phosphates And Their Isomers., *Biochem. J.,* 245:655–660 (1987)). The 400 µl sample was added to a 1.5 ml microfuge tube containing 100 µl of 10 mM EDTA, pH 9.0. This was followed by the addition of 500 µl of 1,1,2 trichlorotrifluroethane/tri-n-octylamine (1:1, v/v). The tubes were vortexed vigorously for 5–7 minutes and then centrifuged at 1500×g for 2 minutes to aid in separation of the three layers. From the top aqueous layer 100 µl were sampled for the determination of $IP_3$ content by the assay described below.

$IP_3$ binding assay: Rat cerebellar membranes were used as the source for the $IP_3$-binding protein in a binding assay modified from published procedures (P. F. Worley, et al, Characterization Of Inositol Triphosphate Receptor binding in brain, *J. Biol. Chem.,* 262:12132–12136 (1987) and D. S. Bredt et al, A Simple, Sensitive, And Specific Radioreceptor Assay For Inositol 1,4,5-Triphosphate In Biological Tissues, *Biochem. Biophys. Res. Commun.*, 159:976–982 (1989)). Membranes were prepared by homogenizing rat cerebella in 30 volumes of homogenization buffer (1 mM EDTA and 1 mM 2-mercaptoethanol in 50 mM Tris.HCl, pH 7.7), using a Tissumizer (Tekmar) at setting 65, for 15 seconds. The homogenate was centrifuges at 39,800×g for 10 minutes at 4°. This procedure was repeated three more times, for a total of four washes. The final pellet was suspended in 30 volumes of $IP_3$ binding buffer (1 mM EDTA and 1 mM 2-mercaptoethanol in 64.3 mM Tris.HCl, pH 9.0) and frozen at −70° until needed.

Binding buffer (350 μl, containing $[^3H]IP_3$ and 50 μl of binding protein homogenate were added to 100 μl of the extracted $IP_3$ samples or known $IP_3$ standards that had been subjected to the extraction procedure as described above. The final concentration of $[^3H]IP_3$ was 1 nM. The tubes were incubated at 0° for 15 minutes and then filtered through Whatman GF/B filters [pre-wet with water and precooled with 2 ml of ice-cold $IP_3$ wash buffer (1 mM EDTA in 50 mM Tris.HCl, pH 9.0)] by using a Brandel cell harvester. The filters were then rapidly washed two times with 1 ml of ice-cold $IP_3$ wash buffer. The amount of $[^3H]IP_3$ trapped on the filters was determined by liquid scintillation counting. The amount of $IP_3$ in the samples was determined by comparison with the standard curve.

When cells expressing the $5-HT_{2B}$ receptor were preincubated with mianserin, methysergide, rauwolscine, or 1-NP before the addition of 5-HT, the 5-HT curves were shifted to the right and the $E_{max}$ values were decreased, relative to 5-HT alone.

$5-HT_{2A}$ and $5-HT_{2C}$ Receptor Binding Activity

The ability of a compound to bind to a $5-HT_{2A}$ or $5-HT_{2C}$ receptor was measured using standard procedures such as that listed below.

Assay Procedure

Membrane preparation from transformed cell lines. Membranes were prepared using AV12 cells (Syrian hamster fibroblast, ATCC no. CRL 9595) stably transformed with the human-$5-HT_{2A}$, or $5-HT_{2C}$ receptor (Wainscott et al., Pharmacological Characteristics Of The Newly Cloned Rat 5-Hydroxytryptamine$_{2F}$ Receptor, *Mol. Pharmacol.*, 48:419–426 (1993)). Briefly, cells expressing the receptor of interest were grown in suspension and harvested by centrifugation. The cells were resuspended in a minimal volume of a hypotonic buffer, 50 mM Tris-HCL, pH 7.4, and frozen at 70° C. until needed. On the day the assay, the suspension was thawed and diluted to 35 ml/0.5×10$^2$ cells, original cell number, with 50 mM Tris-HCl, pH 7.4, and centrifuged at 39,800×g, 4° C. The resulting pellet was resuspended by vortexing and incubated at 37° C. for 10 min, then centrifuged at 39,800×g, 4° C. This pellet was resuspended and centrifuged one more time. To achieve a homogenous membrane suspension, the final pellet was resuspended using a Tissumizer (Tekmar, Cincinnati, Ohio) at setting 75 for 10 to 15 sec. in 67 mM Tris-HCl, pH 7.4, for cells expressing the human or rat $5-HT_{2A}$ receptor or 67 mM Tris-HCl, pH 7.4, containing 13 mM $MgCl_2$ and 0.67 mM EDTA for cells expressing the human $5-HT_{2C}$ receptors.

$5-HT_{2A,2C}$ $[^{125}I]DOI$ binding studies: Human $5-HT_{2A}$ or $5-HT_{2C}$ binding studies were performed essentially as described for $[^3H]5$-HT binding to the $5-HT_{2B}$ receptor with the following exceptions. The assay buffer contained, in final concentration, 10 mM pargyline, 9.75 mM $MgCl_2$, 0.5 mM EDTA, 0.1% sodium ascorbate and 50 mM Tris-HCl, pH 7.4. Incubations were performed at 37° C. for 30 minutes with approximately 40 and 30 mg of protein for the $5-HT_{2A}$ and $5-HT_{2C}$ receptors, respectively, then filtered through Whatman GF/C filters which had been presoaked in 0.5% (w/v) polyethylenimine and precooled with 4 ml of ice-cold wash buffer. The filters were then washed rapidly 4 times with 1 ml of ice-cold wash buffer. The amount of $[^{125}I]DOI$ trapped on the filters was determined using a gamma counter. Nonspecific binding was determined with 10 mm mianserin for $5-HT_{2C}$ and 1 mM ketanserin for $5-HT_{2A}$ receptors. The final concentration of $[^{125}I]DOI$ was approximately 0.07 to 0.15 mM for competition experiments.

Statistical analysis: Nonlinear regression analysis for the saturation and competition curves was performed as described previously (Wainscott et al., Pharmacological Characteristics Of The Newly Cloned Rat 5-Hydroxytryptamine$_{2F}$ Receptor, *Mol. Pharmacol.*, 48:419–426 (1993)). One-way analysis of variance was performed on the $pK_1$ values (i.e., log K., molar) followed by the Tukay-Kramer Honestly Significant Difference test (JMP; SAS Institute Inc., Cary, N.C.). $IC_{50}$ values from the competition curves were converted to $K_d$ values using the Cheng-Prusoff (1973) equation. For $[^{125}I]DOI$-labeled receptors, the $K_d$ of $[^{125}I]DOI$ for the $5-HT_{2A}$ or $5-HT_{2C}$ receptors was determined using a rearrangement of the Cheng-Prusoff equation giving: $K_d = IC\ 50-[L]$, where $IC_{50}$ is the concentration of unlabeled DOI causing 50% inhibition of specific $[^{125}I]DOI$ binding and [I]=the free concentration of $[^{125}I]DOI$.

$IP_3$ Formation in $5-HT_{2A}$ and $5-HT_{2C}$ Transformed Cells $IP_3$ formation assay in $5-HT_{2A}$ and $5-HT_{2C}$ transformed cells was conducted in the same manner as $IP_3$ formation in $5-HT_{2B}$ transformed cells with the exception that human AHSlC-3S cells were used for $5-HT_{2C}$ and human Hu2-3S cells were used for $5-HT_{2A}$.

The following Experiments are for testing the efficacy of the $5-HT_2$ antagonists for treating or ameliorating the symptoms of the common cold or allergic rhinitis.

Experiment #1

Wistar rats (250–350 g, Harlan Sprague Dawley, Indianapolis, Ind.) or Hartley guinea pigs (250–350 g, Charles River Laboratories, Inc., Wilmington, Mass.) are anesthetized with sodium pentobarbital (65 mg/kg or 45 mg/kg, respectively, intraperitoneally).

The femoral vein is exposed and a 50 mg/kg dose of Evans Blue, a fluorescent dye, is injected intravenously (1 mL/kg). Approximately 2 minutes later, a dose of mCPP, alpha-methyl serotonin, or saline is also injected intravenously. The Evans Blue complexes with proteins in the blood and functions as a marker for protein extravasation. Exactly 15 minutes post-injection of the agonist or saline, the animals are killed by exsanguination to rinse out the blood and dye left in the vessels. The posterior vena cava and the aorta of the animals are clamped and the right auricle is cut open to facilitate the process. The exsanguination perfusion is performed by injection of saline (40 mL) into the left ventricle using an approximate infusion rate of 1 mL/sec.

The nasal membrane samples are removed from both sides, blotted dry on a paper towel, and weighed. The samples are then placed in individual tubes containing 3 ml of formamide and incubated at 37° C. for 18–24 hrs. The formamide is separated from the tissue following the incubation and its optical density is read at 620 nm using a Beckmann Model OU-7 spectrophotometer. The optical densities of three known concentrations of Evans Blue dye are used to construct a standard curve from which the Evans Blue dye concentration of the unknown samples is determined. All values are normalized by the weight of the original tissue sample.

Results

Intravenous injection of either mCPP or alpha-methyl serotonin produce an increase in the amount of protein extravasation in the nasal tissue as indicated by the dye Evans Blue when compared to a saline control.

Experiment #2

Wistar rats (250–350 g, Harlan Sprague Dawley, Indianapolis, Ind.) or Hartley guinea pigs (250–350 g, Charles River Laboratories, Inc., Wilmington, Mass.) are anesthetized with sodium pentobarbital (65 mg/kg or 45 mg/kg, respectively, intraperitoneally).

The femoral vein is exposed and a 50 mg/kg dose of Evans Blue combined with a dose of either 6-methyl-1-[(2-chloro-3,4-dimethoxyphenyl)-methyl]-1,2,3,4-tetrahydro-9H-pyrido[3,4-b]indole hydrochloride, spiro-9,9[2-(3,4-dimethoxy)-1,2,3,4-tetrahydronaphthyl]-5-methyl-1,2,3,9-tetrahydro-8H-pyrido indole, 6-methyl-1-[(2-bromo-3,4-dimethoxyphenyl)-methyl]-1,2,3,4-tetrahydro-9H-pyrido[3,4-b]indole and 6-iodo-1-[(3,4-dimethoxyphenyl)-methyl]-1,2,3,4-tetrahydro-9H-pyrido[3,4-b]indole hydrochloride is administered intravenously. Approximately 2 minutes later, a dose of mCPP, alpha-methyl serotonin, or saline is also injected intravenously. The Evans Blue complexes with proteins in the blood and functions as a marker for protein extravasation. Exactly 15 minutes post-injection of the agonist or saline, the animals are killed by exsanguination to rinse out the blood and dye left in the vessels. The posterior vena cava and the aorta of the animals are clamped and the right auricle is cut open to facilitate the process. The exsanguination perfusion is performed by injection of saline (40 mL) into the left ventricle using an approximate infusion rate of 1 mL/sec.

The nasal membrane samples are removed from both sides, blotted dry on a paper towel, and weighed. The samples are then placed in individual tubes containing 3 ml of formamide and incubated at 37° C. for 18–24 hrs. The formamide is separated from the tissue following the incubation and its optical density is read at 620 nm using a Beckmann Model OU-7 spectrophotometer. The optical densities of three known concentrations of Evans Blue dye are used to construct a standard curve from which the Evans Blue dye concentration of the unknown samples is determined. All values are normalized by the weight of the original tissue sample.

Results

Intravenous injection of either mCPP or alpha-methyl serotonin produce an increase in the amount of protein extravasation in the nasal tissue as indicated by the dye Evans Blue when compared to a saline control. 6-methyl-1-[(2-chloro-3,4-dimethoxyphenyl)-methyl]-1,2,3,4-tetrahydro-9H-pyrido[3,4-b]indole hydrochloride, spiro-9,9 [2-(3,4-dimethoxy)-1,2,3,4-tetrahydronaphthyl]-5-methyl-1,2,3,9-tetrahydro-8H-pyrido indole, 6-methyl-1-[(2-bromo-3,4-dimethoxyphenyl)-methyl]-1,2,3,4-tetrahydro-9H-pyrido[3,4-b]indole and 6-iodo-1-[(3,4-dimethoxyphenyl)-methyl]-1,2,3,4-tetrahydro-9H-pyrido[3,4-b]indole hydrochloride dose dependently inhibit the agonist-induced increases in nasal tissue protein extravasation when administered 2 minutes prior to agonist challenge.

Formulations

While it is possible to administer a compound employed in the methods of this invention directly without any formulation, the compounds are usually administered in the form of pharmaceutical compositions comprising a pharmaceutically acceptable excipient and at least one active ingredient (the compound of the present invention). Such compositions contain from about 0.1% by weight to about 90.0% by weight of the present compound. These compositions can be administered by a variety of routes including oral, rectal, transdermal, subcutaneous, intravenous, intramuscular, and intranasal. Many of the compounds employed in the methods of this invention are effective as both injectable and oral compositions. Such compositions are prepared in a manner well known in the pharmaceutical art and comprise at least one active compound. See, e.g., REMINGTON'S PHARMACEUTICAL SCIENCES, (16th ed. 1980).

In making the compositions employed in the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable carriers, excipients and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, tragacanth, gelatin, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compounds of this invention may be delivered transdermally using known transdermal delivery systems and excipients. Most preferably, a compound of this invention is admixed with permeation enhancers including, but not limited to, propylene glycol, polyethylene glycol monolaurate, and azacycloalkan-2-ones, and incorporated into a patch or similar delivery system. Additional excipients including gelling agents, emulsifiers, and buffers may be added to the transdermal formulation as desired.

For oral administration, a compound of this invention ideally can be admixed with carriers and diluents and molded into tablets or enclosed in gelatin capsules.

The compositions are preferably formulated in a unit dosage form, each dosage containing from about 0.05 to about 150 mg, more usually about 1.0 to about 100 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The active compounds are generally effective over a wide dosage range. For example, dosages per day normally fall within the range of about 0.01 to about 30 mg/kg of body weight. In the treatment of adult humans, the range of about 0.1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

In order to more fully illustrate the operation of the present invention, the following formulation examples are provided. The examples are illustrative only, and are not intended to limit the scope of the invention. The formulations may employ as active ingredients (compounds) any of the compounds of the present invention.

Formulation Preparation 1

Hard gelatin capsules containing the following ingredients are prepared:

| Ingredient | Quantity (mg/capsule) |
| --- | --- |
| Active Ingredient(s) | 100.0 |
| Starch | 235.0 |
| Magnesium stearate | 5.0 |

The above ingredients are mixed and filled into hard gelatin capsules in 340 mg quantities.

Formulation Preparation 2

A tablet formula is prepared using the ingredients below:

| Ingredient | Quantity (mg/tablet) |
| --- | --- |
| Active Ingredient(s) | 100.0 |
| Cellulose, microcrystalline | 125.0 |
| Colloidal silicon dioxide | 10.0 |
| Stearic acid | 5.0 |

The components are blended and compressed to form tablets, each weighing 240 mg.

Formulation Preparation 3

A dry powder inhaler formulation is prepared containing the following components:

| Ingredient | Weight % |
| --- | --- |
| Active Ingredient(s) | 5 |
| Lactose | 95 |

The active mixture is mixed with the lactose and the mixture is added to a dry powder inhaling appliance.

Formulation Preparation 4

Tablets, each containing 30 mg of active ingredient, are prepared as follows:

| Ingredient | Quantity (mg/tablet) |
| --- | --- |
| Active Ingredient(s) | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50°–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Preparation 5

Capsules, each containing 40 mg of medicament are made as follows:

| Ingredient | Quantity (mg/capsule) |
| --- | --- |
| Active Ingredient(s) | 40.0 mg |
| Starch | 109.0 mg |
| Magnesium stearate | 1.0 mg |
| Total | 150.0 mg |

The active ingredient, cellulose, starch, and magnesium stearate are blended, passed through a No. 20 mesh U.S. sieve, and filled into hard gelatin capsules in 150 mg quantities.

Formulation Preparation 6

Suppositories, each containing 25 mg of active ingredient are made as follows:

| Ingredient | Amount |
| --- | --- |
| Active Ingredient(s) | 25 mg |
| Saturated fatty acid glycerides to | 2,000 mg |

The active ingredient(s) is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Preparation 7

Suspensions, each containing 50 mg of medicament per 5.0 ml dose are made as follows:

| Ingredient | Amount |
| --- | --- |
| Active Ingredient(s) | 50.0 mg |
| Xanthan gum | 4.0 mg |
| Sodium carboxymethyl cellulose (11%) | 50.0 mg |
| Microcrystalline cellulose (89%) | |
| Sucrose | 1.75 g |
| Sodium benzoate | 10.0 mg |
| Flavor and Color | q. v. |
| Purified water to | 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Preparation 8

Capsules, each containing 15 mg of medicament, are made as follows:

| Ingredient | Quantity (mg/capsule) |
| --- | --- |
| Active Ingredient(s) | 15.0 mg |
| Starch | 407.0 mg |
| Magnesium stearate | 3.0 mg |
| Total | 425.0 mg |

The active ingredient(s), cellulose, starch, and magnesium stearate are blended, passed through a No. 20 mesh U.S. sieve, and filled into hard gelatin capsules in 425 mg quantities.

Formulation Preparation 9

An intravenous formulation may be prepared as follows:

| Ingredient | Quantity |
| --- | --- |
| Active Ingredient(s) | 250.0 mg |
| Isotonic saline | 1000 ml |

Formulation Preparation 10

A topical formulation may be prepared as follows:

| Ingredient | Quantity |
| --- | --- |
| Active Ingredient(s) | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Formulation Preparation 11

Sublingual or buccal tablets, each containing 10 mg of active ingredient, may be prepared as follows:

| Ingredient | Quantity Per Tablet |
| --- | --- |
| Active Ingredient(s) | 10.0 mg |
| Glycerol | 210.5 mg |
| Water | 143.0 mg |
| Sodium Citrate | 4.5 mg |
| Polyvinyl Alcohol | 26.5 mg |
| Polyvinylpyrrolidone | 15.5 mg |
| Total | 410.0 mg |

The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50°–55° C. and the medicament is slowly admixed. The homogenous mixture is poured into forms made of an inert material to produce a drug-containing diffusion matrix having a thickness of about 2–4 mm. This diffusion matrix is then cut to form individual tablets having the appropriate size.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

The type of formulation employed for the administration of the compounds employed in the methods of the present invention may be dictated by the particular compounds employed, the type of pharmacokinetic profile desired from the route of administration and the compound(s), and the state of the patient.

What is claimed is:

1. A method for treating or ameliorating the symptoms of the common cold or allergic rhinitis in a mammal which comprises administering to the mammal an effective amount of a compound or composition having activity as a 5-HT$_{2B}$ receptor antagonist.

2. A method for treating or ameliorating the symptoms of the common cold or allergic rhinitis in a mammal which comprises administering to the mammal an effective amount of a compound of the formula:

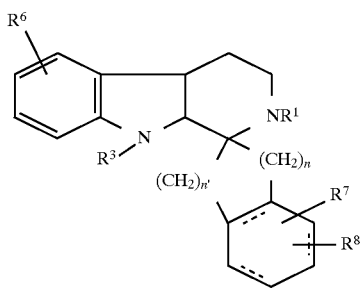

wherein $R^1$ and $R^3$, independently, are hydrogen or $C_1-C_3$ alkyl;

n and n', independently, are 1, 2, or 3;

$R^6$ is hydrogen, $C_1-C_6$ alkyl, $C_2-C_6$ alkenyl, halo, halo$(C_1-C_6)$alkyl, halo$(C_2-C_6)$alkenyl, $COR^5$, $C_1-C_{10}$ alkanoyl, $CO_2R^5$, $(C_1-C_6$alkyl$)_m$amino, $NO_2$, —$SR^5$, or $OR^5$;

$R^7$ and $R^8$, independently, are an $R^6$ group or $C_7-C_{16}$ arylalkyl;

m is 1 or 2;

$R^5$ is hydrogen or $C_1-C_4$ alkyl;

$R^5$ is $C_1-C_4$ alkyl; and

—is optionally a bond; or a pharmaceutically acceptable salt or solvate thereof.

3. A method for treating or ameliorating the symptoms of the common cold or allergic rhinitis in a mammal which comprises administering to the mammal an effective amount of a compound of the formula:

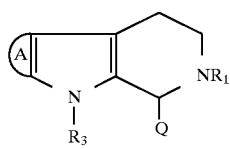

wherein

Q is hydrogen or $(CHR_2)R_4$;

$R_1$, $R_2$ and $R_3$, independently, are hydrogen or $C_1-C_3$ alkyl;

$R_4$ is $C_5-C_8$ cycloalkyl, substituted $C_5-C_8$ cycloalkyl, $C_5-C_8$ cycloalkenyl, substituted $C_5-C_8$ cycloalkenyl, or a bicyclic or substituted bicyclic group;

A is

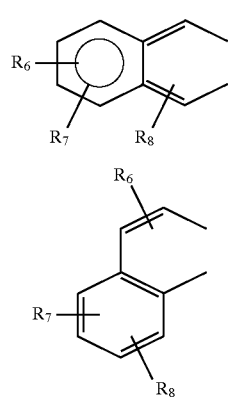

-continued or

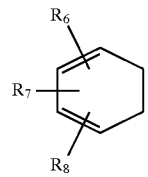

wherein $R_6$ and $R_7$, independently, are hydrogen, $C_1-C_6$ alkyl, $C_2-C_6$ alkenyl, halo, halo$(C_1-C_6)$alkyl, halo$(C_2-C_6)$ alkenyl, $COR_5$, $C_1-C_{10}$ alkanoyl, $CO_2R_5$, $(C_1-C_6$alkyl$)_m$amino, $NO_2$, —$SR_5$, or $OR_5$; or $R_6$ and $R_7$ together with the carbon atoms of group A form a 5-to 8-member carbon ring;

m is 1 or 2;

$R_5$ is hydrogen or $C_1-C_4$ alkyl;

$R_5$, is $C_1-C_4$ alkyl; and $R_8$ is an $R_6$ group, $C_3-C_8$ cycloalkyl, substituted $C_3-C_8$ cycloalkyl, $C_3-C_8$ cycloalkyl-$(C_1-C_3)$alkyl, $C_5-C_8$ cycloalkenyl, substituted $C_5-C_8$ cycloalkenyl, $C_5-C_8$ cycloalkenyl-$(C_1-C_3)$alkyl, or $C_7-C_{16}$ arylalkyl;

or a pharmaceutically acceptable salt or solvate thereof.

4. The method of claim 3 wherein $R_1$ and $R_3$ are hydrogen,

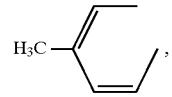

A is and Q is cyclohexylmethyl.

5. A method for treating or ameliorating the symptoms of the common cold or allergic rhinitis in a mammal which comprises administering to the mammal an effective amount of a compound of the formula:

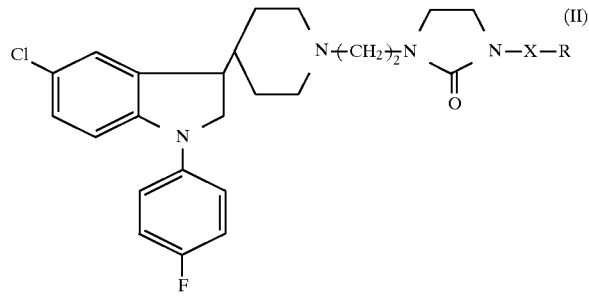

wherein x is CO, CS or $CH_2$;

R is $R^1$, $YR^1$, $NR^2R^3$ or $OC(O)R^1$;

$R^1$ is hydrogen, $C_1-C_{24}$ alkyl, $C_2-C_{24}$ alkenyl, $C_3-C_8$ cycloalkyl, $C_3-C_8$ cycloalkenyl or $C_4-C_{32}$ cycloalk(en)ylalk(en)yl, optionally substituted with one or two hydroxy groups, or phenyl optionally substituted with one or more halogen, trifluoromethyl, $C_1-C_4$ alkyl, $C_1-C_4$ alkoxy, $C_1-C_4$ alkylthio, acyloxy, or cyano substituents;

Y is O or S;

$R^2$ and $R^3$ independently are an $R^1$ group, or $R^2$ and $R_3$ combined together form a four to eight member heterocyclic ring containing from one to three nitrogen atoms and from zero to three oxygen or sulfur atoms;

provided that,
1) R can only be OC(O)R¹ when X is CH₂, and 2) R can only be R¹ when X is CO or CS;
or a pharmaceutically acceptable salt thereof.

6. A method for treating or ameliorating the symptoms of the common cold or allergic rhinitis in a mammal which comprises administering to the mammal an effective amount of a compound of the formula:

(III)

7. A method for treating or ameliorating the symptoms of the common cold or allergic rhinitis in a mammal which comprises administering to the mammal an effective amount of a compound of the formula:

(IV)

wherein
Ar is phenyl; phenyl having at least one halogen, lower alkyl, lower alkoxy, hydroxy, trifluoromethyl, or cyano substituent; or a heteroaromatic group selected from 2-thienyl, 3-thienyl, 2-furanyl, 3-furanyl, 2-oxazolyl, 2-imidazolyl, 2-pyridyl, 3-pyridyl, and 4-pyridyl;
the dotted line is an optional double bond;
X and X¹ independently are hydrogen, halogen, lower alkyl, lower alkoxy, hydroxy, lower alkylthio, lower alkylsulfonyl, lower alkylamino, lower dialkylamino, cyano, trifluoromethyl, or trifluoromethylthio; or
X and X¹ taken together form a 5 to 7 membered carbocyclic ring;

$R^1$ is hydrogen, lower alkyl or alkyl substituted with one or two hydroxy groups;
R is a substituent having the formula:

$$-(CH_2)_n-N-\underset{\underset{W}{\|}}{C}-V^1$$
$$\quad\quad\quad\;\; |$$
$$\quad\quad\quad\; R^3$$

wherein
n is an integer from 2-6 inclusive;
W is oxygen or sulfur;
$V^1$ is $OR^4$, $SR^5$, $CHR^6R^7$, or $NR^8R_9$; and
$R^3$ to $R^9$ independently are hydrogen, lower alkyl, lower alkenyl, cycloalkyl, or lower alkyl or lower alkenyl substituted with one or two hydroxyl groups;
provided that: when X is hydrogen or fluoro, $R^1$ cannot be hydrogen; or
a pharmaceutically acceptable acid addition salt thereof.

8. A method for treating or ameliorating the symptoms of the common cold or allergic rhinitis in a mammal which comprises administering to the mammal an effective amount of a compound of the formula:

(V)

wherein
$R_1$, $R_2$ and $R_3$ independently are hydrogen or $C_1$–$C_6$ alkyl;
X is hydrogen or halogen;
Z is a carbonyl or methylene group; and
$C_9$━━━$C_{10}$ represents a single or a double bond;
or a racemate or acid additional salt thereof.

* * * * *